United States Patent
Wakabayashi

[11] Patent Number: 5,951,576
[45] Date of Patent: Sep. 14, 1999

[54] END-TO-SIDE VASCULAR ANASTOMOSING STAPLING DEVICE

[76] Inventor: Akio Wakabayashi, 16300 Sand Canyon Ave., Irvine, Calif. 92618

[21] Appl. No.: 09/033,035

[22] Filed: Mar. 2, 1998

[51] Int. Cl.[6] .................................................. A61B 17/08
[52] U.S. Cl. ..................... 606/151; 606/219; 227/175.1
[58] Field of Search ................................. 606/138, 151, 606/152, 153, 219; 227/175.1, 176.1, 179.1

[56] References Cited

U.S. PATENT DOCUMENTS

| | | | |
|---|---|---|---|
| 2,935,068 | 5/1960 | Donaldson | 128/348 |
| 4,154,241 | 5/1979 | Rudie | 128/334 C |
| 4,366,819 | 1/1983 | Kaster | 128/334 C |
| 4,368,736 | 1/1983 | Kaster | 128/334 C |
| 4,505,414 | 3/1985 | Filipi | 227/19 |
| 4,523,592 | 6/1985 | Daniel | 128/334 C |
| 4,553,542 | 11/1985 | Schenck et al. | 128/334 R |
| 4,598,712 | 7/1986 | Rebuffat et al. | 128/334 C |
| 4,650,486 | 3/1987 | Chareire | 623/3 |
| 4,657,019 | 4/1987 | Walsh et al. | 128/334 C |
| 4,747,407 | 5/1988 | Liu et al. | 128/334 R |
| 4,747,818 | 5/1988 | Edelschick | 604/8 |
| 4,930,674 | 6/1990 | Barak | 227/179 |
| 4,931,057 | 6/1990 | Cummings et al. | 606/153 |
| 4,966,602 | 10/1990 | Rebuffat et al. | 606/154 |
| 5,188,638 | 2/1993 | Tzakis | 606/153 |
| 5,222,963 | 6/1993 | Brinkerhoff et al. | 606/153 |
| 5,267,940 | 12/1993 | Moulder | 600/16 |
| 5,392,979 | 2/1995 | Green et al. | 227/179 |
| 5,403,333 | 4/1995 | Kaster et al. | 606/219 |
| 5,425,761 | 6/1995 | Lundgren | 623/11 |
| 5,437,684 | 8/1995 | Calabrese et al. | 606/153 |
| 5,443,198 | 8/1995 | Viola | 227/179 |
| 5,456,714 | 10/1995 | Owen | 623/1 |

Primary Examiner—Michael Buiz
Assistant Examiner—Jennifer Maynard
Attorney, Agent, or Firm—Willie Krawitz

[57] ABSTRACT

The stapling device includes an anvil tube with a plurality of radially oriented and outwardly movable segmented arms and associated anvils mounted on the distal end of the segmented arms which are movable within an insertion space. The anvils are conically shaped which enable insertion into a vascular lumen over a guide wire. A staple pusher tube mounting staples at its distal end is mounted externally of the insertion tube. Prior to a stapling procedure, the distal end of the graft is attached to the anvils with a peel-off glue. When the segmented arms are pushed out into a stapling position inside a blood vessel, the anvils open outwardly due to elastic recoil of the segmented arms. The anvils are then stabilized in the stapling position by a centrally inserted expansion rod which is wedged into the core space of the segmented arms. The anvils are pulled back against the vascular wall and the staple pusher is pushed towards the anvils while advancing the staple wires which penetrate the graft and vascular wall and are bent over the anvil to anastomose the graft onto the vascular wall. Following the stapling procedure, the prosthesis is peeled off from the anvils, which are retracted into their folded position, and the device is removed from the patient.

8 Claims, 5 Drawing Sheets

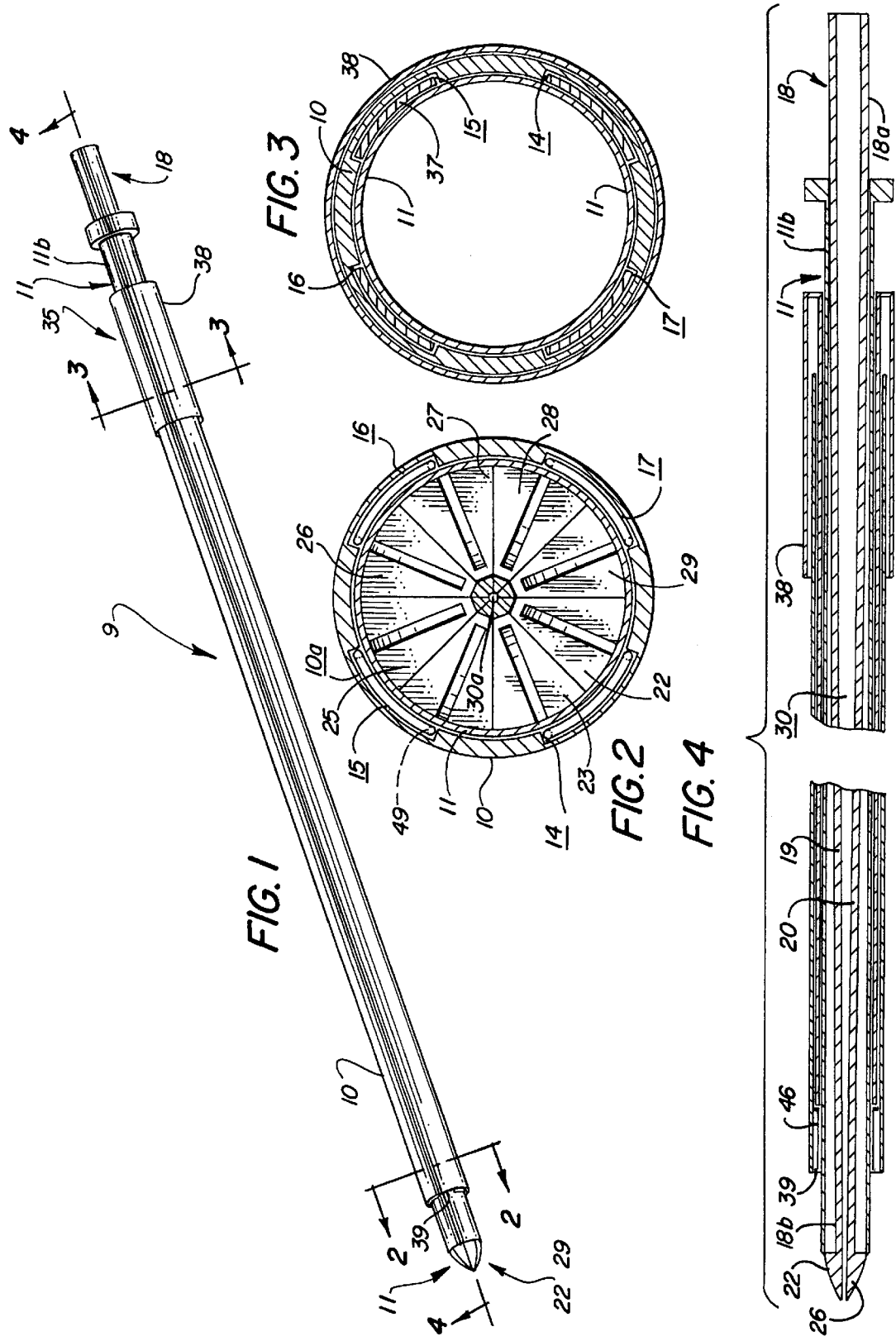

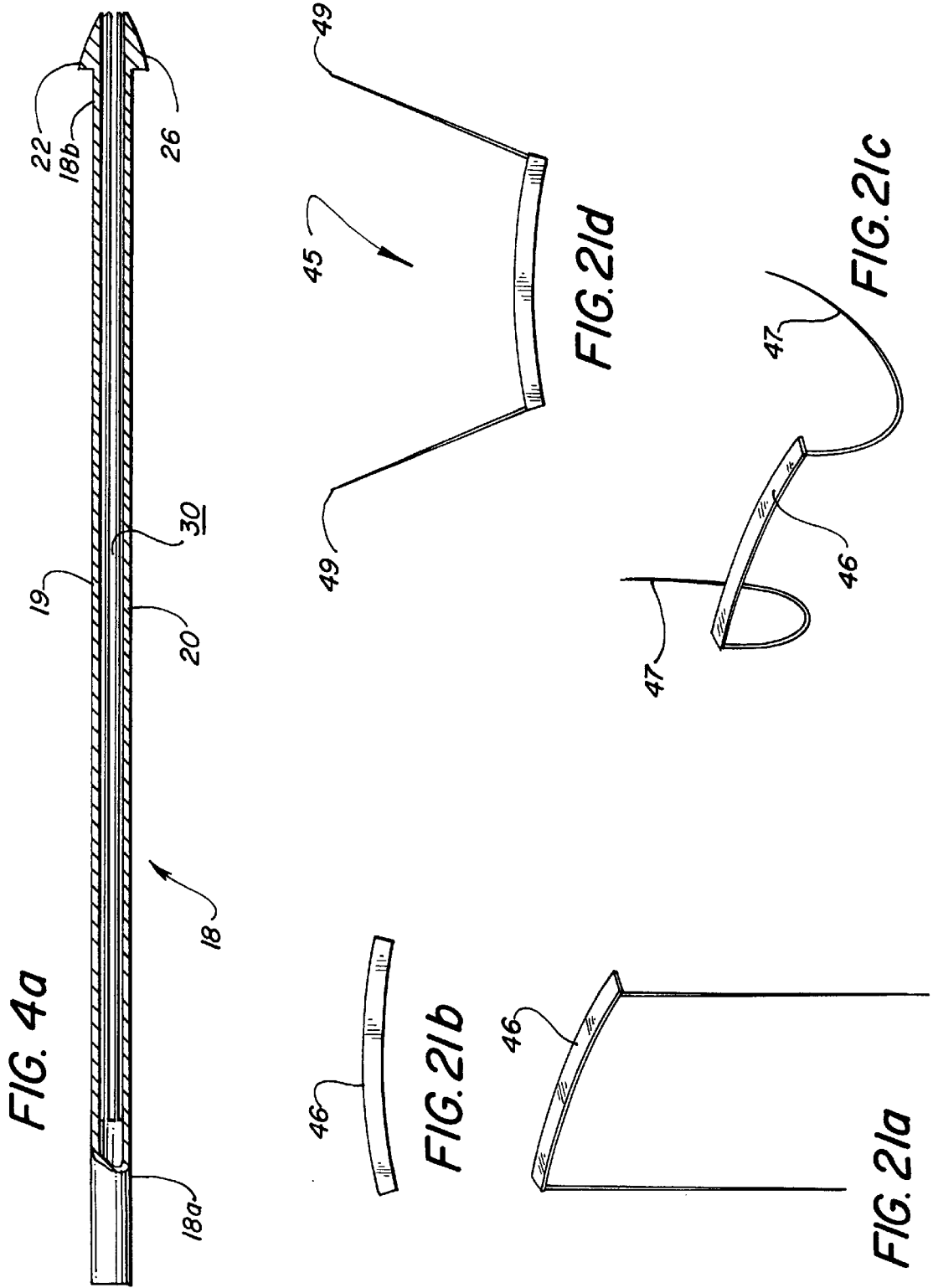

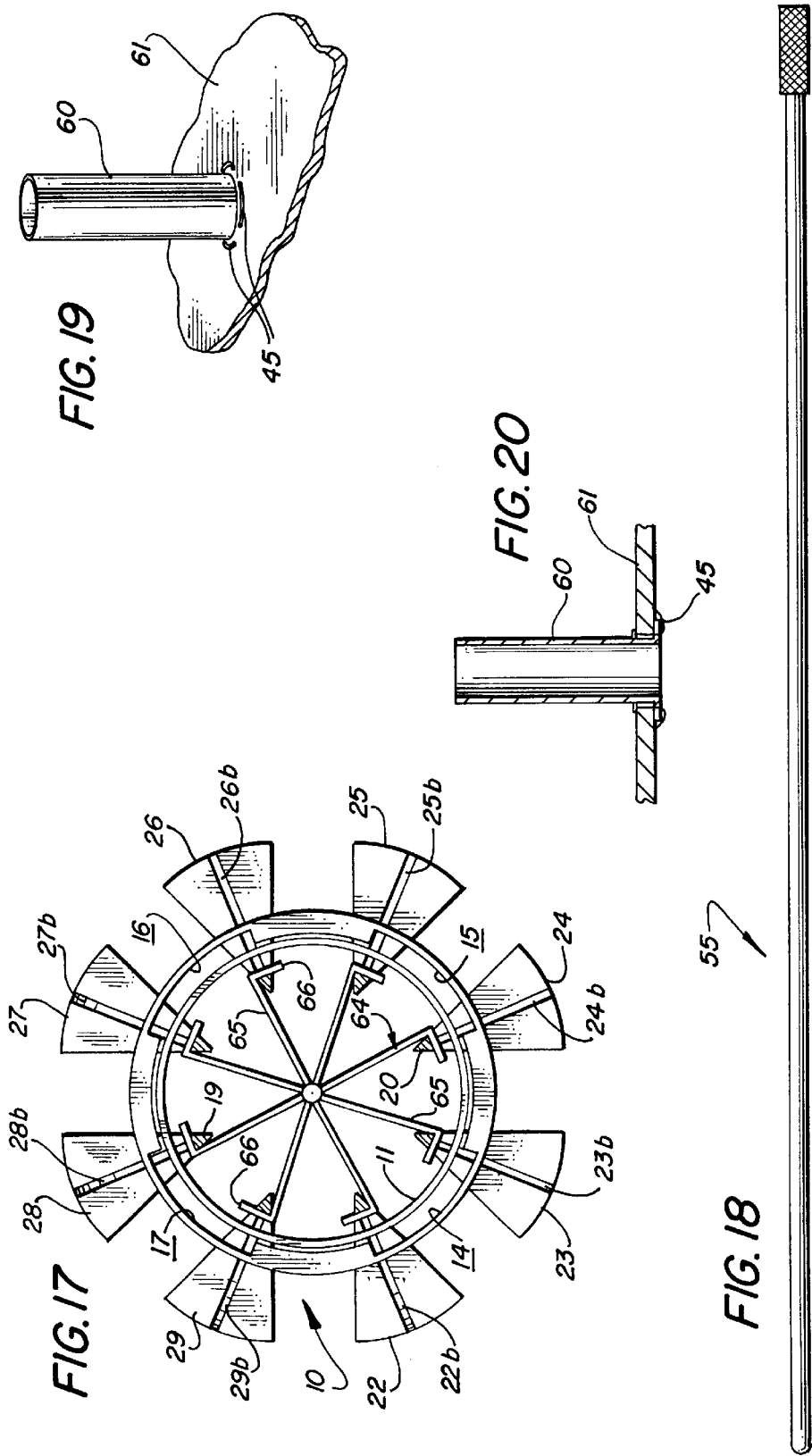

END-TO-SIDE VASCULAR ANASTOMOSING STAPLING DEVICE

BACKGROUND OF THE INVENTION

This invention relates to a new and improved stapling device for an end-to-side vascular anastomosing procedure, and more specifically to a stapling device for use in endoscopic applications, and is intended to eliminate the need for partial clamping the aorta where an end-to-side vascular anastomosis is carried out. A traditional end-to-end vascular anastomoses requires a partial clamping of the aorta followed by a small incision to be made in a partially occluded blood vessel and then suturing the graft to the blood vessel; but this maneuver is extremely difficult when carried out endoscopically.

Publications relating to typical stapling devices and fittings for medical use are described in U.S. Pat. Nos. 4,154, 241; 4,366,819; 4,368,736; 4,505,414; 4,523,592; 4,553, 542; 4,598,712; 4,650,486; 4,657,019; 4,747,407; 4,747, 818; 4,930,674; 4,931,057; 4,966,602; 5,188,638; 5,222, 963; 5,267,940; 5,392,979; 5,403,333; 5,425,761; 5,437, 684; 5,443,198; and, 5,456,714.

However, many of these devices are complicated in their construction and function and cannot be used for endoscopic vascular anastomoses, while others such as described in U.S. Pat. No. 5,403,333 involve use of a ring staple. Ring fittings described in patents in the above list reduce or impair the vein or artery from responding to natural pulsing. In addition, many of the devices described in these patents are not conducive to be used in endoscopic surgery, or are not suitable in end-to-side anastomosis procedures.

There is desired a stapling device suitable for use in endoscopic surgery which is easy to use, reliable, and which enables the artery or blood vessel to respond to natural pulsing.

THE INVENTION

According to the invention, there is provided a stapling device and method which is easy to use in end-to-side anastomosis, reliable, and suitable for endoscopic surgery, which does not require partial clamping the artery or aorta, and does not greatly inhibit pulsing following an anastomosis procedure.

The stapling device comprises a plurality of concentric tubes, including an outer tube, an inner insertion tube securing at its distal end a plurality of expandable and retractable anvils radially mounted at the end of the insertion tube. A pusher tube is mounted between the outer tube and the inner tube for advancing and for firing a plurality of radially mounted, open-ended staple wires against their respective anvils. An expansion rod is provided for radially pushing the anvils outwardly to stabilize the anvils when the insertion tube has been placed within a blood vessel such as a thoracic aorta.

A prosthesis is temporarily attached to the end of the anvils for anastomosing with a blood vessel, and when the pusher tube is fired, the staple wires will penetrate the blood vessel such as a thoracic aorta and prosthesis, and will be bent over their respective anvils; this will anastomose the prosthesis with the blood vessel. When the anastomosing procedure has been completed, the temporary attachment between the prosthesis and the anvils is removed, and the wedge-shaped expansion rod is replaced by a screw clamp or other retraction means. The screw clamp functions to retract the anvils back into the insertion tube, which enables removal of the device from the patient. The free end of the prosthesis is then anastomosed to another portion of the artery by other means. The device of this invention is simple and reliable, and employs reliable staples, besides being easier to use. Also, the staples do not greatly impair or reduce natural artery pulsing at the anastomoses site compared to a ring stapler.

BRIEF DESCRIPTION OF THE DRAWINGS

FIG. 1 is a perspective view of an assembled stapling device according to the invention;

FIG. 2 is a cross sectional plan view of the stapling device taken along lines 2—2 of FIG. 1, the staple pusher being omitted;

FIG. 3 is a cross section view of the stapling device taken along lines 3—3 of FIG. 1;

FIG. 4a is a cross sectional view in side elevation of the anvil shafts and integrally formed anvils;

FIG. 4 is a cross section view in axial section of the stapling device taken along lines 4—4 of FIG. 1;

FIG. 5 is a side elevation view in axial section showing the stapling device, with the tip of the device adjacent the outer side wall of a thoracic aorta just prior to entry of the device through the aorta sidewall, the anvils being retracted into the device, the prosthesis being everted over the end of the stapler and in contact with the anvils;

FIG. 6 is a side elevation view in axial section of the stapling device similar to FIG. 5 after entry of the device through the sidewall of the aorta;

FIG. 7 is a side elevation view in axial section showing the anvils being moved slightly forward into the artery, thereby opening the anvils outwardly after clearing the aorta sidewall;

FIG. 8 is a side elevation view in axial section of the stapling device after insertion of a wedge-shaped core rod into the inner insertion tube to expand the anvils;

FIG. 9 is a side elevation view in axial section of the stapling device showing the expanded anvils being retracted to adjacent the interior wall of the artery and just prior to firing the stapling wires for an anastomosis procedure;

FIG. 10 is a side elevation view in axial section of the stapling device following firing the staples to anastomose the prosthesis and artery wall;

FIG. 11 is a side elevation view in axial section of the stapling device following the anastomosis procedure showing the device being advanced slightly into the artery to clear the interior of the side wall;

FIG. 12 is a side elevation view in axial section of the stapling device after the wedge-shaped core rod has been removed from between the anvils;

FIG. 13 is a side elevation view in axial section of the stapling device showing retraction of the anvils to an unfolded position and prior to retraction of the anvils into the inner tube;

FIG. 14 is a side elevation view in axial section of the stapling device showing the anvils being retracted into the device and commencement of removing the device from the anastomosed prosthesis and artery;

FIG. 17 is a cross section view of the stapling device showing the hooks of screw clamps contacting the anvil shafts preparatory to retracting the anvil shafts into the inner tube;

FIG. 18 is an external view in side elevation showing a wedge-shaped rod for the device;

FIG. 19 is a perspective view of an anastomosed prosthesis and artery wall, the top portion of the staples being shown engaging the artery wall;

FIG. 20 is a sectional view in side elevation showing the staples after being fired to anastomose an artery wall with a prosthesis; and, FIGS. 21a–c show four views of a staple of this invention, as follows:

FIG. 21a is a perspective view of a staple prior to firing;

FIG. 21b is a plan view of FIG. 21a;

FIG. 21c is a perspective view of a staple after it has been fired in an anastomosis procedure; and, FIG. 21d is a plan view of FIG. 21c.

DESCRIPTION OF THE PREFERRED EMBODIMENTS

Figure 15:
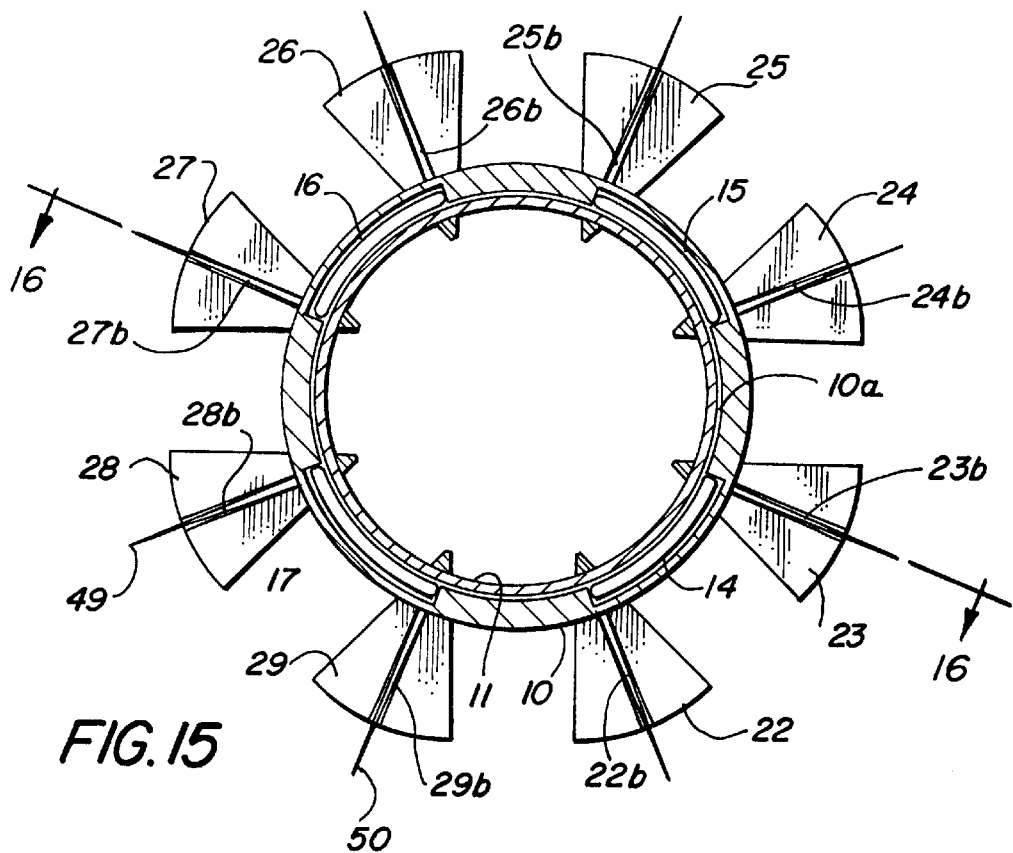
FIG. 15 is a cross section plan view of the stapling device showing the expanded anvils and the location of the anvil slots and inserted staples which have been fired.
Figure 16:
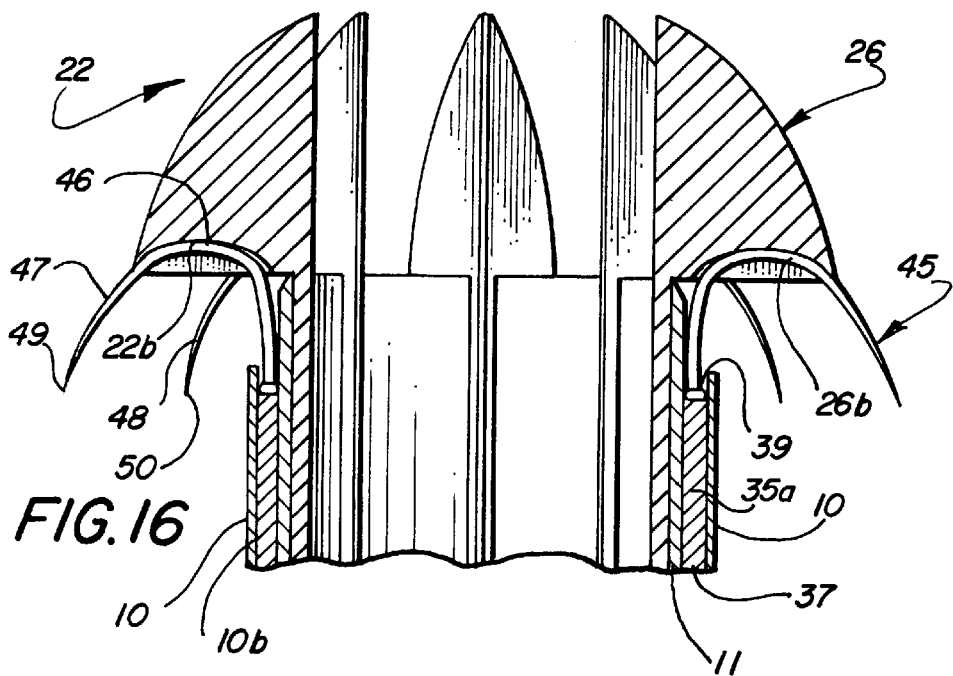
FIG. 16 is an external, perspective view of taken along lines 16—16 of FIG. 15.

The stapling device 9 of the invention is shown generally in FIGS. 1–4, providing an outer tube 10 defining an inner wall 10a and an inner tube 11 defining distal and proximal ends 11a and 11b, respectively. The inner wall 10a of the outer tube 10 defines four curved, longitudinal slots 14, 15, 16 and 17 along which similarly shaped staple wire pushers are advanced and for subsequently firing staple wires; various details of the wire pushers are shown in FIG. 16. Four staple wires are separately press fitted into these longitudinal slots, the staples and fitting procedure being described, infra, in connection with FIGS. 15, 16 and 21.

A medical grade steel anvil element 18 defining a hollow, proximal end 18a and a distal end 18b is interfitted in the inner tube 11 and can be movably advanced therein. The anvil element is segmented into eight, flexible, expandable or compressible sections integrally formed or attached to the proximal end, two sections 19 and 20 being shown in FIGS. 4, 4a and 6. The flexible sections are separated to form a space 30 which enables insertion of the device along a guide wire (not shown) to the aorta, and the space 30 also permits the subsequent insertion and retraction of an expansion rod 55, as shown in FIGS. 8–11.

Anvil tips 22–29 are mounted at the distal ends 18b of each flexible section, and when closed or retracted, as shown in FIGS. 1, 2 and 4, the anvil tips are compressed into a tightly compact configuration having a wedge, arrow or conical shape. This compact configuration when compressed to form the conical shape reduces the space 30 to a central pin hole size 30a through which a guide wire (not shown) is threaded, and movement of the device takes place along the guide wire. The conical shape also facilitates entry of the anvils into an artery or aorta.

Figure 7:
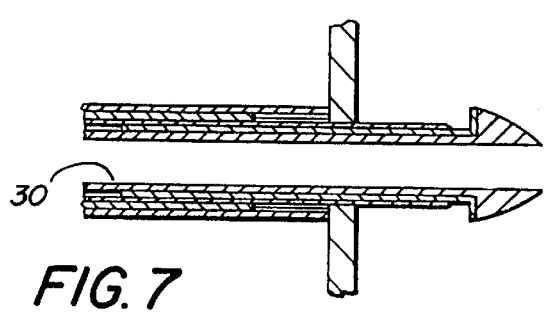
Figure 12:
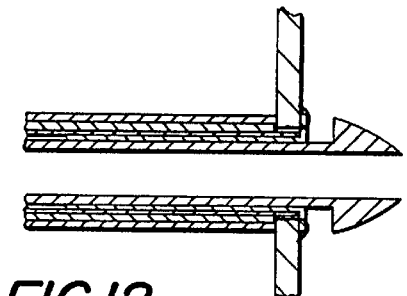
Figure 8:
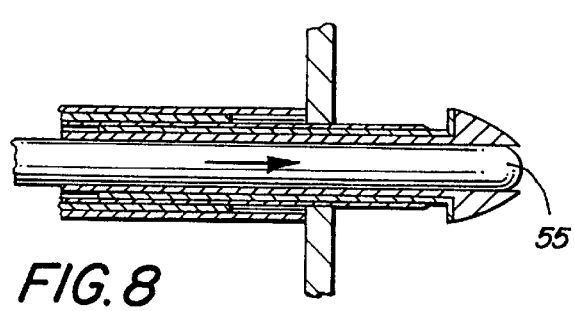

Longitudinal movement of the inner tube 11 advances the anvils into an artery over a guide wire, and initial expansion of the anvils from the closed or retracted position due to forward movement of the anvil element 18 will occur due to their flexibility, and is shown in FIG. 7. As indicated, subsequent stabilization and support of the anvils using an expansion rod 55 is shown in connection with FIGS. 8–11, infra.

As shown in FIGS. 1, 4 and 16, a staple pusher 35 is slidably mounted on the outer tube 10 and comprises a staple pushing element 37, and an attached handle 38. A space 39 is formed between the outer tube 36 and the inner tube 11, and hence longitudinal movement of handle 38 towards the anvils will move the staple pushing element 37 along this space 39. Longitudinal movement of the staple pusher 35 will advance four staples 45 towards the distal end 35a of the staple pusher, and into the slots 14–17 adjacent the anvils, and anvil slots 22b–29b.

As described in FIGS. 21a–d, each staple 45 is open-ended, and typically is constructed of titanium. As shown in FIGS. 15, 16 and 21, an individual staple comprises a central portion 46, side portions 47, and ends 49. The staples of this invention are simple and relatively easy to use, and when installed in an anastomosis procedure, do not greatly inhibit arterial pulsing.

The structure of the anvils 22–29 is illustrated in FIGS. 2, 15, 16 and 18, and as shown in FIGS. 1 and 15, are wedge-shaped to enable retraction into the tightly compact and conical shape shown in FIG. 1. FIGS. 15, 16 and 17, show the anvils are paired into sets 22–23, 24–25, 26–27 and, 28–29, the anvils being disposed adjacent to their respective slots 14, 15, 16 and 17 along the inner wall 10a of the outer tube 10. Anvil slots 22b to 29b are defined along a central axis of each anvil to engage the side portions 47 of the staples 45, while the staple ends 49 project from the anvil slot ends.

With the guide wire removed, the anvil tips are pushed out of the inner tube 11 when the anvil element 18 is advanced, and an expansion rod 55 (FIG. 18) is inserted into the space 30 formed by the flexible sections, such as 19 and 20. The inherent flexibility of these metal anvil sections e.g., 19 and 20 due to elastic recoil changes their configuration from a compressed form into an outward stapling position. In this outward stapling position, the expansion rod 55 will support and stabilize the anvil sections during a stapling procedure when the anvils are inserted inside an aorta or artery, and this is illustrated in FIGS. 8–11.

Figure 5:
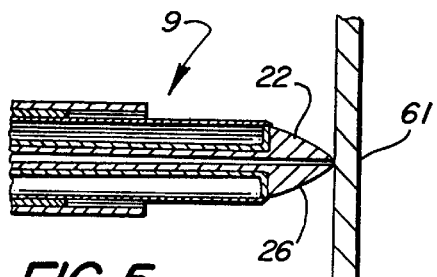
FIGS. 5–14 are views showing the stapling device of this invention during an anastomosis procedure, as follows.
Figure 6:
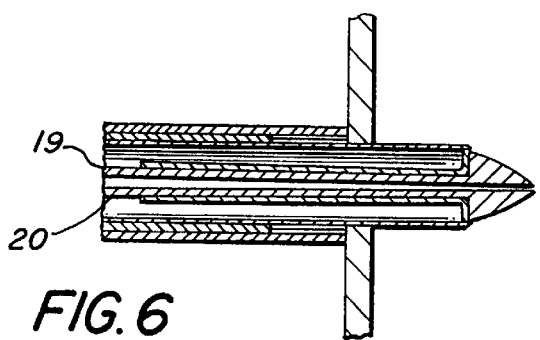

The end-to-side anastomosing procedure utilizing the stapling device 9 of this invention is generally shown in FIGS. 5–14. A prosthesis 60 is temporarily attached to the end of each anvil by peel-off glue, and the tubular structure enables the stapling device 9 to be advanced into a patient through a trocar (not shown) and eventual penetration of the artery 61, as shown in FIGS. 5 and 6. When the anvils have penetrated the artery, and released from the inner tube 11 due to elastic recoil, they are then further advanced to clear the inner tube. The expansion rod 55 is inserted into space 30 between the flexible sections (e.g., 19 and 20) of the anvil (FIGS. 8, et seq.) thereby expanding, supporting and stabilizing the anvils.

Figure 10:
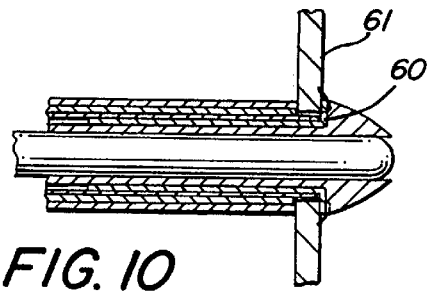
Figure 11:
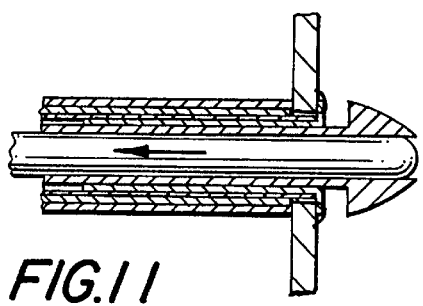
Figure 9:
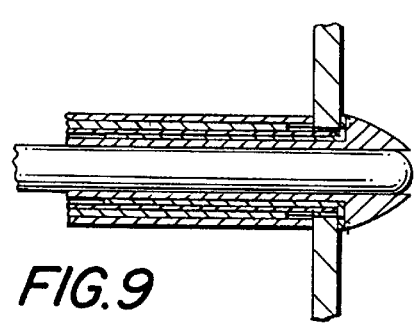

The device is then retracted against the inner wall of the aorta, shown in FIG. 9, and the staples are fired to anastomose the end of the prosthesis 60 with the sidewall of the artery 61, as shown in FIGS. 10, 19 and 20. The firing procedure changes the shape of a staple from the linear configuration shown in FIGS. 4 and 21b, to the curved shape shown in FIGS. 21c and 21d, as the staple is bent into and anastomose the prosthesis with the artery. Following the anastomosis procedure, the anvils are advanced to clear the stapling device from the interior wall of the artery, as shown in FIG. 11, and removal of the expansion rod 55, shown in FIG. 12.

Figure 13:
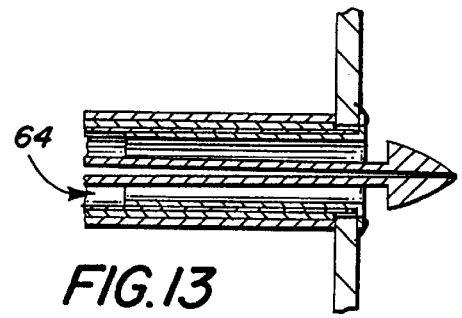
Figure 14:
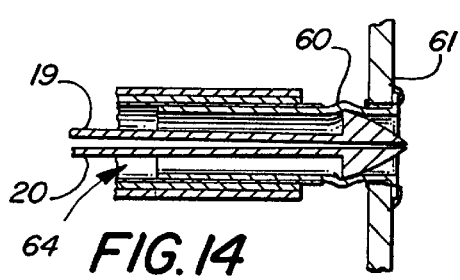

Following removal of the expansion rod 55, the flexible sections are retracted and compressed to their original closed or retracted configuration, as shown in FIGS. 1, 2 and 4. This is accomplished, as shown in FIGS. 13, 14 and 17, by means of a retraction tool 64. The retraction tool provides a plurality of screw actuated arms 65 having end hooks 66 which are inserted into the stapling device to engage the anvils. The arms 65 retract the anvils into their original, closed configuration, shown in FIG. 13. In this closed configuration, the stapling device 9 is then retracted from the anastomosed prosthesis and artery and removed from the patient. The free end of the prosthesis is then temporarily clamped off prior to conclusion of the by-pass procedure.

The stapling device of this invention is compact and tubular in shape, which enables insertion by means of a trocar, and provides greater maneuverability. Moreover, the open-ended type of staple employed in the device enables an easy installation, and this open-ended configuration also permits a more natural arterial pulsing following an anastomosing procedure, rather than imposing a radial clamp on an aorta or artery.

I claim:

1. A stapling device for end-to-side vascular anastomoses of an aorta or artery, comprising:
   a.) an outer tube defining inner and outer walls, the inner wall defining a plurality of radial slots formed longitudinally along the tube length;
   b.) an inner tube defining distal and proximal ends and mounted for longitudinal movement within the outer tube, a radial space being defined between the outer and inner tubes;
   c.) an anvil tube movably mounted within the inner tube, the anvil tube defining distal and proximal ends, the proximal end providing a hollow holder, and a plurality of expandable and compressible, flexible, segmented arms associated with the distal end of the holder;
   d.) an anvil mounted distally at each end of the segmented arms, compression of the arms confining the arms and anvils into the inner tube for advance or retraction, thereby forming a closed insertion space between the arms and anvils, the arms and anvils being expandable beyond the distal end of the inner tube, the anvils when closed, facilitating entry with a surrounding prosthesis into the aorta or artery, for end-to-side anastomosis, the arms and anvils expanding open for an anastomosis procedure when advanced beyond the end of the inner tube;
   e.) an expansion rod for insertion through the hollow holder of the anvil tube, and opening the closed insertion space between the arms and each respective anvil, thereby, expanding the insertion space and stabilizing and supporting the anvils in an open, stapling configuration for an anastomosis procedure when the respective anvils are positioned in the aorta or artery; and,
   f.) a staple pusher tube mounted for slidable movement along the radial space between the inner and outer tubes and along the radial slots of the outer tube, and to advance and fire a plurality of open-shaped staples along the radial slots of the outer tube, the staple firing causing a staple to be shaped over a respective anvil, and to close, penetrate, and be spaced circumferentially of the prosthesis, thereby, anastomosing the prosthesis with a sidewall of the aorta or artery, without radial clamping.

2. The stapling device of claim 1, defining an anvil slot along each anvil, an anvil slot being positioned at either end of each radial slot, and upon firing, a staple is driven along adjacent anvil slots and into a corresponding radial slot, and bent into the prosthesis and aorta or artery, to form an anastomoses therebetween.

3. The stapling device of claim 1, in which the anvils when closed define a configuration including conical, wedge or an arrow shape.

4. The stapling device of claim 3, in which each staple defines straight sides prior to firing, and when the staples are fired, the straight sides become curved.

5. A method for end-to-side anastomoses of an aorta or artery, comprising providing inner and outer tubes defining a plurality of radial slots formed longitudinally therebetween and along the tube lengths; the inner and outer tubes defining distal and proximal ends and mounted for longitudinal movement therebetween, and a radial space being defined between the outer and inner tubes; an anvil tube movably mounted within the tubes, the anvil tube defining distal and proximal ends, the proximal end providing a hollow holder, and a plurality of expandable and compressible, flexible, segmented arms integrally formed with the hollow holder; an anvil mounted distally at each end of the segmented arms, compression of the segmented arms confining the arms and anvils into the inner and outer tubes for advance or retraction, thereby forming a closed insertion space between the arms and anvils, the arms and anvils being expandable beyond the distal ends of the tubes; the method, comprising: i. when the anvils are closed, entering with a surrounding prosthesis into the aorta or artery for end-to-side anastomoses; ii. expanding the anvils for an anastomoses procedure by advancing the anvils beyond the end of the tubes; iii inserting an expansion rod through the hollow holder of the anvil tube and into the closed insertion space between the arms and anvils; iv. thereby, expanding the insertion space and stabilizing and supporting the anvils in an open, stapling configuration for an anastomosis procedure when the anvils are positioned in the aorta or artery; v. sliding a staple pusher tube along the radial space between the inner and outer tubes and along the radial slots between the tubes, and; vi. advancing and firing plurality of open-shaped staples along the radial slots between the tubes, the staple firing causing a staple to be shaped over a respective anvil, and to close, penetrate, and be spaced circumferentially of the prosthesis; thereby, anastomosing the prosthesis with a sidewall of the aorta or artery, without radial clamping.

6. The method of claim 5, defining an anvil slot along each anvil, an anvil slot being positioned at either end of a radial slot, and upon firing, each staple is driven along adjacent anvil slots and into a corresponding radial slot, and bent into the prosthesis and aorta or artery, to form an anastomoses therebetween.

7. The method of claim 5, in which the anvils when closed define a configuration including conical, wedge or an arrow shape.

8. The method of claim 7, in which each staple defines straight sides prior to firing, and the staple firing forms curved staple sides.

* * * * *